United States Patent [19]

Janssens et al.

[11] Patent Number: 5,360,807
[45] Date of Patent: Nov. 1, 1994

[54] SUBSTITUTED THIAZOLYL AND SUBSTITUTED PYRIDINYL DERIVATIVES

[75] Inventors: Frans E. Janssens, Bonheiden; Francois M. Sommen, Wortel; Gaston S. M. Diels, Ravels, all of

[73] Assignee: Janssen Pharmaceutica N.V., Beerse,

[21] Appl. No.: 197,579

[22] Filed: Feb. 17, 1994

Related U.S. Application Data

[63] Continuation of Ser. No. 157,845, Nov. 24, 1993, abandoned, which is a continuation of Ser. No. 17,363, Feb. 11, 1993, abandoned, which is a continuation of Ser. No. 723,878, Jul. 1, 1991, abandoned, which is a continuation-in-part of Ser. No. 554,325, Jul. 19, 1990, abandoned.

[51] Int. Cl.$^5$ ............ A61K 31/445; A61K 31/44; C07D 211/14; C07D 211/40
[52] U.S. Cl. ................ 514/318; 514/322; 514/323; 546/193; 546/199; 546/201
[58] Field of Search ............ 514/318, 322, 323; 546/193, 199, 201

[56] References Cited

U.S. PATENT DOCUMENTS

| | | | |
|---|---|---|---|
| 4,695,575 | 9/1987 | Janssens et al. | 514/322 |
| 4,988,689 | 1/1991 | Janssens et al. | 514/212 |
| 5,041,448 | 8/1991 | Janssens et al. | 514/266 |

*Primary Examiner*—Robert T. Bond
*Assistant Examiner*—Y. N. Gupta

[57] ABSTRACT

Substituted thiazolyl and substituted pyridinyl derivatives of formula

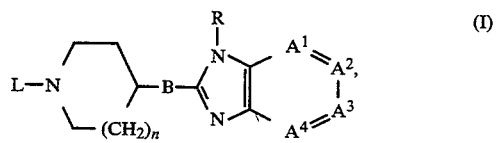

the pharmaceutically acceptable acid addition salts and the stereochemically isomeric forms thereof, wherein $-A^1=A^2-A^3=A^4-$ is a bivalent radical having the formula

| | |
|---|---|
| $-CH=CH-CH=CH-$ | (a-1), |
| $-N=CH-CH=CH-$ | (a-2), |
| $-CH=N-CH=CH-$ | (a-3), |
| $-CH=CH-N=CH-$ | (a-4), |
| $-CH=CH-CH=N-$ | (a-5), |
| $-N=CH-N=CH-$ | (a-6) |
| or | |
| $-CH=N-CH=N-$ | (a-7); |

B represents $NR^1$, $CH_2$, O, S, SO or $SO_2$ wherein $R^1$ is hydrogen or $C_{1-4}$-alkyl;
R is a radical of formula;

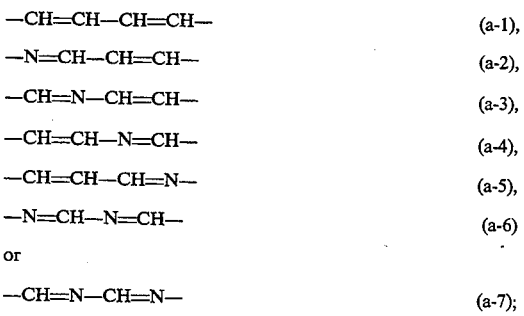

wherein D is $C_{1-4}$alkanediyl; $R^2$ is $C_{1-6}$alkyl;
n is 0, 1 or 2;
L is hydrogen; $C_{1-12}$alkyl; $C_{3-6}$cycloalkyl; $C_{3-6}$alkenyl optionally substituted with aryl; $C_{1-6}$alkylcarbonyl; $C_{1-6}$alkyloxycarbonyl; arylcarbonyl; aryl$C_{1-6}$alkyloxycarbonyl; or a radical of formula

| | |
|---|---|
| $-Alk-R^3$ | (c-1); |
| $-Alk-Y-R^4$ | (c-2); |
| $-Alk-Z^1-C(=X)-Z^2-R^5$ | (c-3); |
| or | |
| $-CH_2-CHOH-CH_2-O-R^6$ | (c-4); | have antiallergic properties. Compositions containing the same and methods of treating warm-blooded animals suffering from allergic diseases.

4 Claims, No Drawings

SUBSTITUTED THIAZOLYL AND SUBSTITUTED PYRIDINYL DERIVATIVES

CROSS-REFERENCE TO RELATED APPLICATION

This is a continuation of application Ser. No. 07/723,878, filed Jul. 1, 1991, now abandoned, which is a continuation-in-part of U.S. Ser. No. 554,325 filed Jul. 19, 1990 now abandoned, which is a continuation of application Ser. No. 08/017,363, filed Feb. 11, 1993, now abandoned, This is a continuation of application Ser. No. 157,845, filed Nov. 24, 1993, now abandoned.

BACKGROUND OF THE INVENTION

In U.S. Pat. Nos. 4,556,600; 4,634,704; 4,695,569; 4,695,575; 4,588,722; 4,835,161; 4,897,401 and in EP-A-0,026,415 and 0,297,661 there are disclosed benzimidazole and imidazopyridine substituted piperidine derivatives as antihistaminics and serotomin antagonists.

1. Description of the Invention

The present invention is concerned with novel substituted thiazolyl and substituted pyridinyl derivatives having the formula:

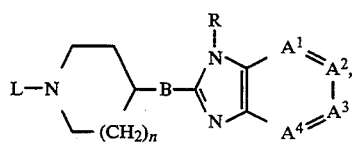  (I)

the pharmaceutically acceptable acid addition salts and the stereochemically isomeric forms thereof, wherein —$A^1$=$A^2$—$A^3$=$A^4$— is a bivalent radical having the formula —CH=CH—CH=CH—  (a-1), —N=CH—CH=CH—  (a-2), —CH=N—CH=CH—  (a-3), —CH=CN—N=CH—  (a-4), —CH=CH—CH=N—  (a-5), —N=CN—N=CH—  (a-6)

or

—CH=N—CH=N—  (a-7);

wherein one or two hydrogen atoms in said radicals (a-1) to (a-7) may each independently be replaced by halo, $C_{1-6}$alkyl, $C_{1-6}$alkyloxy, hydroxy or trifluoromethyl;

B represents $NR^1$, $CH_2$, O, S, SO or $SO_2$ wherein $R^1$ is hydrogen or $C_{1-4}$alkyl;

R is a radical of formula;

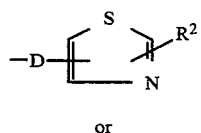  (b-1)

or

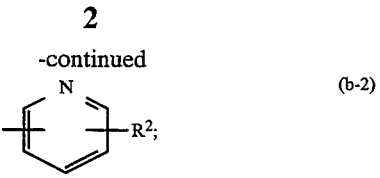  (b-2)

wherein D is $C_{1-4}$alkanediyl;

$R^2$ is $C_{1-6}$alkyl;

n is 0, 1 or 2;

L is hydrogen; $C_{1-12}$alkyl; $C_{3-6}$cycloalkyl; $C_{3-6}$alkenyl optionally substituted with aryl; $C_{1-6}$alkylcarbonyl; $C_{1-6}$alkyloxycarbonyl; arylcarbonyl; aryl$C_{1-6}$alkyloxycarbonyl; or a radical of formula —Alk—$R^3$  (c-1);

—Alk—Y—$R^4$  (c-2);

—Alk—$Z^1$—C(=X)—$Z^2$—$R^5$  (c-3);

or

—$CH_2$—CHOH—$CH_2$—O—$R^6$  (c-4);

wherein $R^3$ is cyano, aryl or Het;

$R^4$ is hydrogen, aryl, Het or $C_{1-6}$alkyl optionally substituted with aryl or Het;

$R^5$ is hydrogen, aryl, Her or $C_{1-6}$alkyl optionally substituted with ary, 1 or Het;

$R^6$ is aryl or naphthalenyl;

Y is O, S, $NR^7$; said $R^7$ being hydrogen, $C_{1-6}$alkyl or $C_{1-6}$alkylcarbonyl;

$Z^1$ and $Z^2$ each independently are O, S, $NR^8$ or a direct bond; said $R^8$ being hydrogen or $C_{1-6}$alkyl;

X is O, S or $NR^9$; said $R^9$ being hydrogen, $C_{1-6}$alkyl or cyano; each Alk independently is $C_{1-6}$alkanediyl;

each Het is:

(i) an optionally substituted five- or six-membered heterocyclic ting containing 1, 2, 3 or 4 heteroatoms selected from oxygen, sulfur and nitrogen, provided that no more than 2 oxygen and/or sulfur atoms are present;

(ii) an optionally substituted five- or six-membered heterocyclic ring containing 1 or 2 heteroatoms selected from oxygen, sulfur and nitrogen, being fused with an optionally substituted five- or six-membered ring through 2 carbon atoms or 1 carbon and 1 nitrogen atom, containing in the remainder of the fused ting only carbon atoms; or (iii) an optionally substituted five- or six-membered heterocyclic ring containing 1 or 2 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;

wherein Her being a monocyclic ring system may be optionally substituted with up to 4 substituents; and wherein Het being a bicyclic ring system may be optionally substituted with up to 6 substituents, said substituents being selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, $C_{1-6}$alkyloxy$C_{1-6}$alkyl, $C_{1-6}$alkyloxycarbonyl$C_{1-6}$alkyl, hydroxy, mercapto, hydroxy$C_{1-6}$alkyl, $C_{1-6}$alkylcarbonyloxy, aryl, aryl$C_{1-6}$alkyl, carboxyl, $C_{1-6}$alkylaminocarbonylamino, arylaminocarbonylamino, oxo or thio;

each aryl is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

In the compounds of formula (I) where $R^3$, $R^4$ or $R^5$ is Het, said Het may be partly or completely saturated, or unsaturated. The compounds of formula (I) wherein Her is partly saturated or unsaturated and is substituted with hydroxy, mercapto or amino, may also exist in their tautomeric forms. Such forms although not explicitly indicated hereinabove, are intended to be included within the scope of the invention.

As used in the foregoing definitions halo is generic to fluoro, chloro, bromo and iodo; $C_{1-4}$alkyl defines straight and branch chained saturated hydrocarbon radicals having from 1 to 4 carbon atoms such as, for example, methyl, ethyl, propyl, 1-methylethyl, butyl, 1,1-dimethylethyl, 1-methylpropyl, 2-methylpropyl; $C_{1-6}$alkyl defines $C_{1-4}$alkyl radicals as defined hereinabove and the higher homologs thereof having 5 or 6 carbon atoms; $C_{1-12}$alkyl defines $C_{1-4}$alkyl radicals as defined hereinabove and the higher homologs thereof having from 5 to 12 carbon atoms; $C_{3-6}$cycloalkyl is genetic to cyclopropyl, cyclobutyl, cyclopentyl and cyclohexyl; $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and when a $C_{3-6}$alkenyl is substituted on a heteroatom, then the carbon atom of said $C_{3-6}$alkenyl connected to said heteroatom preferably is saturated; $C_{1-4}$alkanediyl defines bivalent straight and branch chained saturated hydrocarbon radicals having from 1 to 4 carbon atoms such as, for example, methylene, 1,2-ethanediyl, 1,3-propanediyl, 1,4-butanediyl and the branched isomers thereof; $C_{1-6}$alkanediyl defines $C_{1-4}$alkanediyl radicals as defined hereinabove and the higher homologs thereof having 5 or 6 carbon atoms such as, for example, 1,5-pentanediyl, 1,6-hexanediyl and the branched isomers thereof.

The pharmaceutically acceptable acid addition salts as mentioned herein above comprise the therapeutically active non-toxic acid addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid, and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt also comprises the hydrates and solvent addition forms which the compounds of formula (I) are able to form. Examples of such forms are e.g. hydrams, alcoholates and the like.

The compounds of this invention may have several asymmetric carbon atoms in their structure. Each of these chiral centers may be indicated by the stereochemical descriptors R and S.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral acids. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereoselective methods of preparation. These methods will advantageously employ enantiomerically pure starting materials. Stereochemically isomeric forms of the compounds of formula (I) are obviously intended to be included within the scope of the invention.

In particular, the radical Het as defined herein above may be selected from pyridinyl, optionally substituted with one or two substituents each independently selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, aryl$C_{1-6}$alkyl and carboxyl; pyridinyloxide, optionally substituted with nitro; pyrimidinyl, optionally substituted with one or two substituents each independently selected from halo, amino, $C_{1-6}$alkylamino, aryl$C_{1-6}$alkylamino, hydroxy, $C_{1-6}$alkyl, $C_{1-6}$alkyloxy, $C_{1-6}$alkylthio and aryl$C_{1-6}$alkyl; pyridazinyl, optionally substituted with $C_{1-6}$alkyl or halo; pyrazinyl, optionally substituted with halo, amino or $C_{1-6}$alkyl; thienyl, optionally substituted with halo or $C_{1-6}$alkyl; furanyl, optionally substituted with halo or $C_{1-6}$alkyl; pyrrolyl, optionally substituted with $C_{1-6}$alkyl; thiazolyl, optionally substituted with $C_{1-6}$alkyl, $C_{1-6}$alkyloxycarbonyl, aryl or aryl$C_{1-6}$alkyl; imidazolyl, optionally substituted with one or two substituents each independently selected from $C_{1-6}$alkyl, aryl$C_{1-6}$alkyl and nitro; tetrazolyl, optionally substituted with $C_{1-6}$alkyl; 1,3,4-thiadiazolyl, optionally substituted with $C_{1-6}$alkyl or amino; 5,6-dihydro-4H-1,3-thiazin-2-yl, optionally substituted with $C_{1-6}$alkyl; 4,5-dihydrothiazolyl, optionally substituted with $C_{1-6}$alkyl; oxazolyl, optionally substituted with $C_{1-6}$alkyl; 4,5-dihydro-5-oxo-1H-tetrazolyl, optionally substituted with $C_{1-6}$alkyl; 1,4-dihydro-2,4-dioxo-3(2H)-pyrimidinyl, optionally substituted with $C_{1-6}$alkyl; 3,4-dihydro-4-oxopyrimidinyl or 4,5-dihydro-4-oxopyrimidinyl, both radicals optionally substituted with up to 3 substituents selected from $C_{1-6}$alkyl, amino, $C_{1-6}$alkylaminocarbonylamino, arylaminocarbonylamino, aryl$C_{1-6}$alkylamino and $C_{1-6}$alkylamino; 2,3-dihydro-3-oxopyridazinyl; 2-oxo-3-oxazolidinyl; pyrrolidinyl; piperidinyl; morpholinyl; thiomorpholinyl; dioxanyl, optionally substituted with $C_{1-6}$alkyl; indolyl, optionally substituted with hydroxy or $C_{1-6}$alkyl; quinolinyl, optionally substituted with hydroxy or $C_{1-6}$alkyl; quinazolinyl, optionally substituted with hydroxy or $C_{1-6}$alkyl; quinoxalinyl, optionally substituted with $C_{1-6}$alkyl; phthalazinyl, optionally substituted with halo; 1,3-dioxo-1H-isoindol-2(3H)-yl; 2,3-dihydro-3-oxo-4H-benzoxazinyl and 2,3-dihydro-1,4-benzodioxinyl, both being optionally substituted with $C_{1-6}$alkyl or halo; 2-oxo-2H-1-benzopyranyl and 4-oxo-4H-1-benzopyranyl, both being optionally substituted with $C_{1-6}$alkyl; 3,7-dihydro-1,3-dimethyl-2,6-dioxo-1H-purin-7-yl, optionally substituted with $C_{1-6}$alkyl; 6-purinyl, and a bicyclic heterocyclic radical of formula

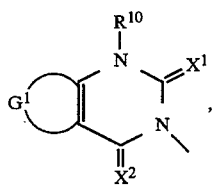 (d-1)

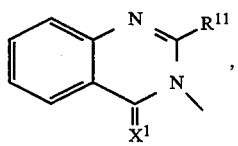 (d-2)

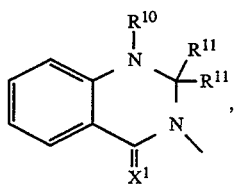 (d-3)

(d-4)

(d-5)

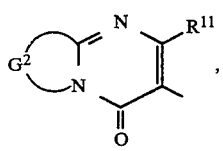 (d-6)

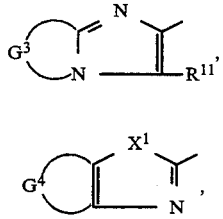 (d-7)

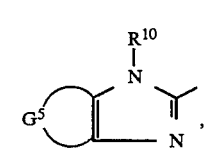 (d-8)

wherein
$X^1$ and $X^2$ each independently are O or S;
each $R^{10}$ independently is hydrogen, $C_{1-6}$alkyl, aryl$C_{1-4}$alkyl, $C_{1-6}$alkyloxy$C_{1-6}$alkyl, hydroxy$C_{1-6}$alkyl or $C_{1-6}$alkyloxycarbonyl;

each $R^{11}$ independently is hydrogen, $C_{1-6}$alkyl, hydroxy, mercapto, $C_{1-6}$alkyloxy, $C_{1-6}$alkylthio, halo or $C_{1-6}$alkyloxycarbonyl$C_{1-6}$alkyl;

$G^1$ is —CH=CH—CH=CH—; —S—CH=CH— or —N=CN—NH—;

$G^2$ is —CH=CH—CH=CH—, —(CH$_2$)$_4$-, —S-(CH$_2$)$_2$—, —S-(CH$_2$)$_3$—, —S—CH=CH—, —CH=CH—O—, —NH—(CH$_2$)$_2$—, —NH—(CH$_2$)$_3$—, —NH—CH=CH—, —NH—N=CH—CH$_2$—, —NH—CH=N— or —NN—N=CH—;

$G^3$ is —CH=CH=CH—, —CH$_2$—NH—(CH$_2$)$_2$—, —S—CH=CH—, —S—(CH$_2$)$_3$—, —N=CH—CH=CH—, —CH=N—CH=CH—, —CH=CH—N=CH—, —CH=CH—CH=N—, —N=CH—N=CH— or —CH=N—CH=N—;

$G^4$ is —CH=CH—CH=CH—, —CH$_2$—NH—(CH$_2$)$_2$—, —N=CH—CH=CH—, —CH=N—CH=CH—, —CH=CN—N=CH—, —CH=CH—CH=N—, —N=CN—N=CH— or —CH=N—CH=N—;

$G^5$ is —CH=CH—CH=CH—, —N=CH—CH=CH—, —CH=N—CH=CH—, —CH=CN—N=CH—, —CH=CH—CH=N—, —N=CN—N=CH— or —CH=N—CH=N—;

$G^6$ is —CH=CH—CH=CH—, —N=CH—CH=CH—, —CH=N—CH=CH—, —CH=CN—N=CH—, —CH=CH—CH=N—, —N=CN—N=CH— or —CH=N—CH=N—;

wherein one or two hydrogen atoms in the benzene part of the radicals of formula (d-2) or (d-3) or one or two hydrogen atoms in said radicals $G^1$, $G^2$, $G^3$, $G^4$, $G^5$ or $G^6$ may be replaced by $C_{1-6}$alkyl, $C_{1-6}$alkylthio, $C_{1-6}$alkyloxy or halo, when connected to a carbon atom; or by $C_{1-6}$alkyl, $C_{1-6}$alkyloxycarbonyl or aryl$C_{1-6}$alkyl when connected to a nitrogen atom; and aryl is as defined hereinabove.

Aryl as used in the definition of $R^3$, $R^4$ and $R^5$, in particular is phenyl optionally substituted with halo, $C_{1-6}$alkyl, hydroxy or $C_{1-6}$alkyloxy; aryl as used in the definition of $R^6$ in particular is phenyl optionally substituted with halo.

A particular subgroup among the compounds of formula (I) comprises those compounds of formula (I) wherein —$A^1$=$A^2$—$A^3$=$A^4$— is a bivalent radical of formula (a-1) or (a-2); another particular subgroup among the compounds of formula (I) comprises those compounds of formula (I) wherein —$A^1$=$A^2$—$A^3$=$A^4$— is a bivalent radical having a formula (a-3) through (a-5); wherein one or two hydrogen atoms in said radicals (a-1) to (a-5) may each independently be replaced by $C_{1-6}$alkyloxy or hydroxy.

Particularly interesting compounds are those compounds of any of the former groups or subgroups wherein B is NR$^2$, O or CH$_2$; and/or L is hydrogen, $C_{1-6}$alkyl, $C_{1-6}$alkylcarbonyl, $C_{1-6}$alkyloxycarbonyl, or a radical of formula (c-1), (c-2), (c-3) or (c-4).

More particularly interesting compounds are those particularly interesting compounds of formula (I) wherein B is NH or CH$_2$; and/or n is 1 or 2; and/or R is a radical of formula:

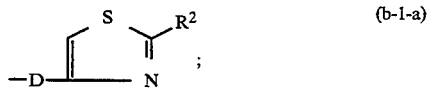 (b-1-a)

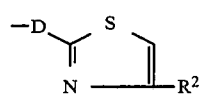 (b-1-b)

or

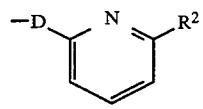 (b-2-a)

Preferred compounds are any of the above defined groups of compounds wherein —$A^1$=$A^2$—$A^3$=$A^4$— is a bivalent radical of formula —CH=CH—CH=CH— (a-1) or —N=CH—CH=CH— (a-2); wherein one or two hydrogen atoms in said radicals (a-1) or (a-2) may each independently be replaced by $C_{1-6}$alkyloxy or hydroxy; D is $CH_2$; and/or L is hydrogen; $C_{1-6}$alkyl; a radical of formula (c-1) wherein $R^3$ is aryl or Het; a radical of formula (c-2) wherein Y is NH or O and $R^4$ is aryl or Het; or a radical of formula —Alk—N-H—CO—Het (c-3-a); wherein each Het is pyridinyl, optionally substituted with amino or $C_{1-6}$alkyl; pyrimidinyl, optionally substituted with amino or $C_{1-6}$alkyl; pyrazinyl, optionally substituted with amino; thienyl; furanyl; thiazolyl, optionally substituted with $C_{1-6}$alkyl; imidazolyl, optionally substituted with $C_{1-6}$alkyl; tetrazolyl, optionally substituted with $C_{1-6}$alkyl; 1,3,4-thiadiazolyl, optionally substituted with $C_{1-6}$alkyl or amino; oxazolyl, optionally substituted with $C_{1-6}$alkyl; 4,5-dihydro-5-oxo-1H-tetrazolyl, optionally substituted with $C_{1-6}$alkyl; 1,4-dihydro-2,4-dioxo-3(2H)-pyrimidinyl; 3,4-dihydro-4-oxopyrimidinyl optionally substituted with up to 3 substituents selected from $C_{1-6}$alkyl, amino and $C_{1-6}$alkylamino; 2-oxo-3-oxazolidinyl; indolyl, optionally substituted with $C_{1-6}$alkyl; phthalazinyl; 2-oxo-2H-1-benzopyranyl; 3,7-dihydro-1,3-dimethyl-2,6-dioxo-1H-purin-7-yl, optionally substituted with $C_{1-6}$alkyl; 6-purinyl, or a bicyclic heterocyclic radical of formula (d-1) to (d-8) as defined hereinabove, wherein $R^{10}$ and $R^{11}$ each independently are hydrogen or $C_{1-6}$alkyl and in the radicals (d-2) and (d-3), $X^1$ is O, and;

each aryl is unsubstituted phenyl; phenyl substituted with 1 or 2 substituents each independently selected from halo, hydroxy, nitro, cyano, trifluoromethyl, $C_{1-6}$alkyl and $C_{1-6}$alkyloxy; and optionally further substituted with a third substituent selected from halo, $C_{1-6}$alkyl or $C_{1-6}$alkyloxy.

More preferred compounds are those preferred compounds wherein L is hydrogen or $C_{1-3}$alkyl.

Further more preferred compounds are those preferred compounds wherein L is a radical of formula —Alk—$R^3$ (c-1) wherein $R^3$ is 4-methoxyphenyl; 4-hydroxyphenyl; thienyl; thiazolyl optionally substituted with $C_{1-6}$alkyl; oxazolyl; 4,5-dihydro-1H-tetrazolyl optionally substituted with $C_{1-6}$alkyl; 2,3-dihydro-2-oxo-benzimidazol-1-yl; 1,4-dihydro-2,4-dioxo-3(2H)-pyrimidinyl; thienyl; 2-oxo-2H-1-benzopyranyl or $R^3$ is a radical of formula

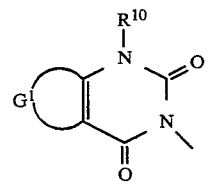 (d-1-a)

or

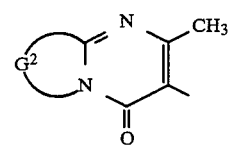 (d-4-a)

wherein $G^1$, $G^2$ and $R^{10}$ are as defined hereinabove.

Still other more preferred compounds are those preferred compounds wherein L is a radical of formula —Alk—Y—$R^4$ (c-2) wherein Y is NH or O and $R^4$ is thiazolyl, pyridinyl, 1,3,4-thiadiazolyl optionally substituted with $C_{1-6}$alkyl or amino, pyrimidinyl optionally substituted with amino, 6-purinyl, 3,4-dihydro-4-oxopyrimidinyl, phthalazinyl or 3H-imidazo[4,5-c]pyridin-2-yl.

Interesting compounds within the present invention are those compounds of formula (I) wherein —$A^1$=$A^2$—$A^3$=$A^4$— represents a bivalent radical of formula —CH=CH—CH=CH— (a-1) or —N=CH—CH=CH— (a-2); B represents NH, $CH_2$ or O; R represents a radical of formula —$CH_2$—⟨S,R²,N⟩ (b-1-c)

—$CH_2$—⟨S,R²,N⟩ (b-1-d)

—$CH_2$—⟨S,N,R²⟩ (b-1-e)

or

—$CH_2$—⟨N,R²⟩ (b-2-b)

$R^2$ represents $C_{1-4}$alkyl; n is 1; L represents hydrogen, $C_{1-4}$alkyl, $C_{1-4}$alkyloxycarbonyl or a radical of formula —Alk—$R^3$(c-1), —Alk—Y—$R^4$ (c-2) or —Alk—$Z^1$—C(=X)—$Z^2$—$R^5$ (c-3); Alk represents $C_{1-4}$alkanediyl; $R^3$ represents phenyl, $C_{1-4}$alkyloxyphenyl or a radical of formula

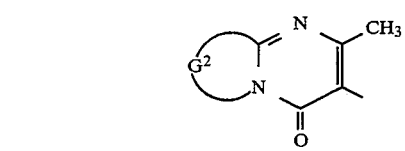

wherein $G^2$ represents —CH=CH—CH=CH—, —S—$(CH_2)_3$—, —S—$(CH_2)_2$— or —S—CH=CH—; Y represents O or NH; $R^4$ represents hydrogen, $C_{1-4}$alkyl or pyrimidinyl; $R^5$ represents $C_{1-4}$alkyl; $Z^1$ represents NH; $Z^2$ represents O; and X represents O.

Particularly interesting compounds are those interesting compounds wherein B represents NH or $CH_2$; $R^2$ represents methyl; L represents $C_{1-4}$alkyl or a radical of formula —Alk—$R^3$ (c-1), —Alk—Y—$R^4$ (c-2) or —Alk—$Z^1$—C(=X)—$Z^2$—$R^5$ (c-3); Alk represents $C_{2-4}$alkanediyl; $R^3$ represents 4-methoxyphenyl or a radical of formula

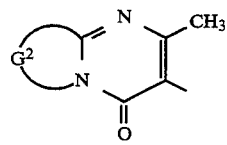

wherein $G^2$ represents —CH=CH—CH=CH—, —S—$(CH_2)_3$—, —S—$(CH_2)_2$— or —S—CH=CH—; Y represents O or NH; and $R^4$ represents $C_{1-4}$alkyl or 2-pyrimidinyl.

Other particularly interesting compounds are those interesting compounds wherein B represents NH or $CH_2$; $R^2$ represents methyl; L represents hydrogen, $C_{1-4}$alkyloxycarbonyl, phenylmethyl, hydroxyethyl or aminoethyl.

Especially interesting compounds are those particularly interesting compounds wherein L represents methyl or a radical of formula —Alk—$R^3$ (c-1), Alk represents 1,2-ethanediyl and $R^3$ represents 4-methoxyphenyl or a radical of formula

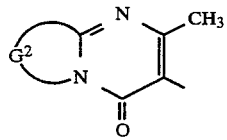

wherein $G^2$ represents —CH=CH—CH=CH—, —S—$(CH_2)_3$—, —S—$(CH_2)_2$— or —S—CH=CH—.

In order to simplify the structural representation of some of the compounds and intermediates in the following preparations the moiety containing the in-fidazole group fused to a benzene, pyridine or pyrimidine ring will hereinafter be represented by the symbol Q.

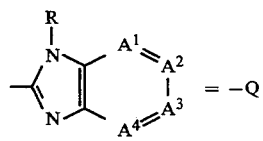

The compounds of formula (I) can generally be prepared by reacting an intermediate of formula (II) with an appropriately substituted diamine of formula (III).

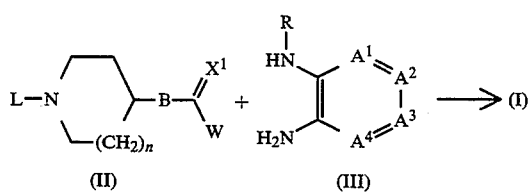

In this and the following reaction schemes W represents an appropriate reactive leaving group such as, for example, halo, e.g. chloro, bromo or iodo; $C_{1-6}$alkyloxy; $C_{1-6}$alkylthio, aryloxy or arylthio; and. $X^1$ denotes O, S or NH.

The derivatives of formula (II) wherein B is $CH_2$ and W is halo may be generated in situ, for example, by halogenating the corresponding carboxylic acid with thionyl chloride, phosphorous trichloride, phosphoryl chloride, polyphosphoric acid and the like reagents. The reaction of (II) with (III) may be conducted in a suitable reaction-inert solvent such as, for example, a hydrocarbon, e.g., benzene, hexane and the like; an ether, e.g., 1,1'-oxybisethane, tetrahydrofuran and the like; a ketone, e.g., 2-propanone, 2-butanone and the like; an alcohol, e.g., methanol, ethanol, 2-propanol, 1-butanol and the like; a halogenated hydrocarbon, e.g., trichloromethane, dichloromethane and the like; an organic acid, e.g., acetic acid, propanoic acid and the like; a dipolar aprotic solvent e.g., N,N-dimethylformamide, N,N-dimethylacetamide and the like; or a mixture of such solvents. Depending upon the nature of the solvent and W it may be appropriate to add to the reaction mixture a base such as is commonly employed in the an of conducting N-alkylation reactions and/or a iodide salt such as an alkali metal iodide. Elevated temperatures and stirring may enhance the reaction rate.

In some instances the reaction of (II) with (III) may first yield an intermediate of formula (II-a) which subsequently may be cyclized to the desired compound of formula (I), either in situ or, if desired, after isolation and purification.

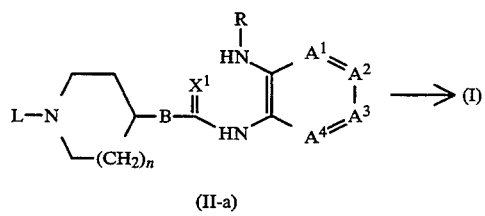

The compounds of formula (I) can also be prepared by reacting an intermediate of formula (IV) with an intermediate of formula (V) following art-known substitution reaction procedures. In (IV) and hereinafter, M is hydrogen when B is other than $CH_2$, or M represents an alkali or earth alkaline metal such as, for example, lithium or magnesium, when B represents $CH_2$.

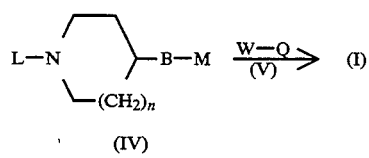

Similarly, the compounds of formula (I) can also be prepared by reacting an intermediate of formula (VI) with an intermediate of formula (VII) wherein M has the previously defined meaning. In formula (VI) and hereinafter $W^1$ represents an appropriate leaving group such as, for example, halo, e.g., chloro, bromo and the like; or a sulfonyloxy group such as, for example, methanesulfonyloxy, 4-methylbenzenesulfonyloxy and the like.

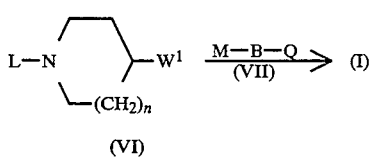

(VI)

The compounds of formula (I) wherein B is —$CH_2$-, said compounds being represented by formula (1-a), can also be prepared by reacting an intermediate of formula (VIII) with an intermediate of formula (IX) or alternatively, by reacting an intermediate of formula (X) with an intermediate of formula (XI).

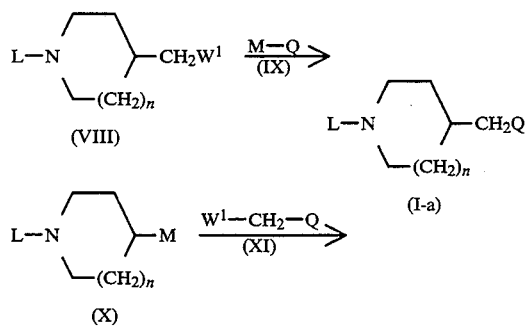

The reactions of (IV), (VI), (VIII) and (X) with respectively (V), (VII), (IX) and (XI) may conveniently be conducted in an appropriate reaction-inert solvent such as for example, an aromatic hydrocarbon, e.g., benzene, methylbenzene and the like; an ether, e.g. 1,4-dioxane, 1,1'-oxybisethane, tetrahydrofuran and the like; a halogenated hydrocarbon, e.g. trichloromethane and the like; N,N-dimethylformamide; N,N-dimethylacetamide; nitrobenzene; dimethylsulfoxide; 1-methyl-2-pyrrolidinone and the like; and when M is hydrogen, said solvent may also be a $C_{1-6}$alkanol, e.g., methanol, ethanol, 1-butanol and the like; a ketone, e.g., 2-propanone, 4-methyl-2-pentanone and the like. In some instances, particularly when B is a heteroatom, the addition of an appropriate base such as, for example, an alkali metal carbonate or hydrogen carbonate, e.g., sodium carbonate, sodium hydrogen carbonate and the like; sodium hydride; or an organic base such as, for example, N,N-diethylethanamine or N-(1-methylethyl)-2-propanamine and/or the addition of an iodide salt, preferably an alkali metal iodide. may be appropriate. Somewhat elevated temperatures and stirring may enhance the rate of the reaction. A convenient alternative for reacting the intermediate of formula (IV) wherein —B—M represents —$NH_2$ with the reagents of formula (V) comprises stirring and heating the reactants in the presence of copper metal in a reaction-inert solvent such as described hereinbefore, in particular a dipolar aprotic solvent, e.g. N,N-dimethylformamide, N,N-dimethylacetamide and the like.

The compounds of formula (I) wherein B is —$NR^1$—, said compounds being represented by formula (I-b), can also be prepared by reacting an intermediate of formula (XII) with an intermediate of formula (VII) wherein B-M represents a radical —$NR^1$—H, said intermediate being represented by formula (VII-a), following art-known reductive N-alkylation procedures.

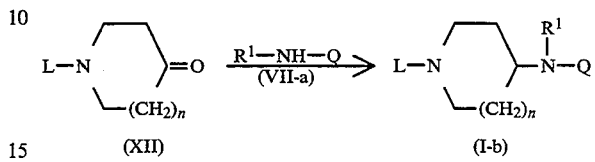

The reaction of (XII) with (VII-a) can conveniently be carried out by mixing the reactants in a suitable reaction-inert solvent with an appropriate reductant. Preferably, the ketone of formula (XII) is first reacted with the intermediate of formula (VII-a) to form an enamine, which optionally may be isolated and further purified, and subsequently reducing said enamine. Suitable solvents are, for example, water;, $C_{1-6}$alkanols, e.g., methanol, ethanol, 2-propanol and the like; ethers, e.g., 1,4-dioxane and the like; halogenated hydrocarbons, e.g., trichloromethane and the like; dipolar aprotic solvents, e.g., N,N-dimethylformamide, N,N-dimethylacetamide, dimethylsulfoxide and the like; or a mixture of such solvents. Appropriate reductants are for example, metal or complex metal hydrides, e.g., sodium borohydride, sodium cyanoborohydride, lithium aluminum hydride and the like. Alternatively, hydrogen in the presence of a suitable catalyst such as, for example, palladium-on-charcoal, platinum-on-charcoal and the like may be used as reductant. In order to prevent the undesired further hydrogenation of certain functional groups in the reactants and the reaction products it may be advantageous to add an appropriate catalyst poison to the reaction mixture such as, for example, thiophene and the like.

The compounds of formula (I-b) wherein $R^1$ is H, said compounds being represented by formula (I-b-1), can also be prepared by a cyclodesulfurization reaction of an appropriate thiourea of formula (II-a) wherein $X^1$ is S, said thiourea being represented by formula (II-a-1), which may be formed in situ by condensing an isothiocyanate of formula (XIII) with a diamine of formula (III).

Said cyclodesulfurization reaction may be carded out by reacting (II-a-1) with an appropriate alkyl halide, preferably iodomethane, in a suitable reaction-inert organic solvent such as a $C_{1-6}$alkanol, e.g., methanol, ethanol, 2propanol and the like. Alternatively, said cyclodesulfurization reaction may also be carded out by the reaction of (II-a-1) with an appropriate metal oxide or salt such as, for example, a Hg(II) or Pb(II) oxide or salt, e.g., HgO, $HgCl_2$, $Hg(OAc)_2$, PbO or $Pb(OAc)_2$ in an appropriate solvent following art-known procedures. In some instances it may be appropriate to supplement the reaction mixture with a small amount of sulfur. Also methanediimides, especially dicyclohexylcarbodiimide may be used as cyclodesulfurizing agents.

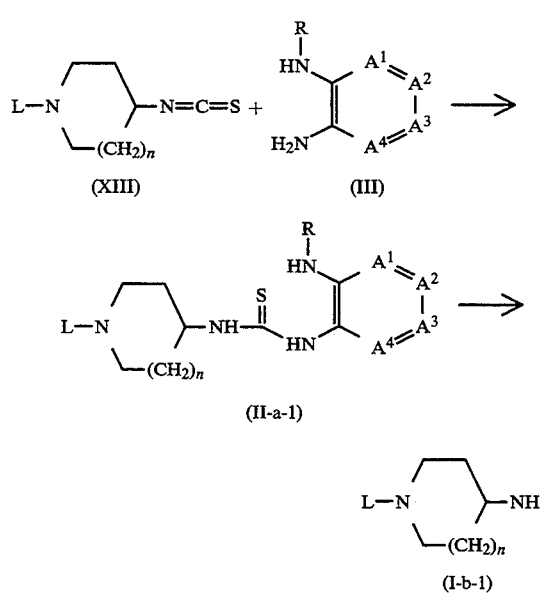

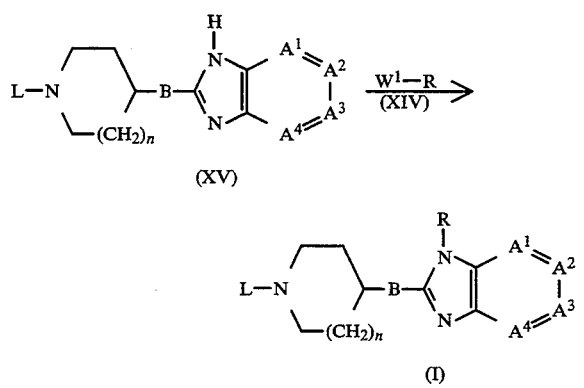

The compounds of formula (I) can also be prepared by N-alkylating an intermediate of formula (XV) with an appropriate alkylating reagent of formula (XIV).

Said N-alkylation reaction can conveniently be conducted in a reaction-inert solvent such as, for example, water; an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethylsulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Additionally, it may be advantageous to conduct said N-alkylation under an inert atmosphere such as, for example, oxygen-free argon or nitrogen.

Alternatively, said N-alkylation may be carded out by applying art-known conditions of phase transfer catalysis reactions. Said conditions comprise stirring the reactants with an appropriate base and optionally under an inert atmosphere as described hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts.

The compounds of formula (I) wherein L is other than hydrogen, said L being represented by $L^1$, and said compounds being represented by formula (1-d) can also be prepared by N-alkylating a compound of formula (I) wherein L is hydrogen, said compound being represented by (I-e), with an alkylating reagent of formula (XVI).

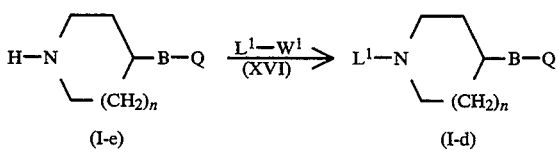

Said N-alkylation is conveniently conducted following art-known N-alkylation procedures as described hereinabove for the preparation of (I) from (XIV) and (XV).

The compounds of formula (I-d) wherein L is $C_{3-6}$cycloalkyl, $C_{1-12}$alkyl, a radical of formula (c-1), (c-2) or (c-3), said radicals being represented by the radical $L^2H$— and said compounds by formula (1-d-1) can also be prepared by the reductive N-alkylation reaction of (1-e) with an appropriate ketone or aldehyde of formula $L^2{=}O$ (XVII), said $L^2{=}O$ being an intermediate of formula $L^2H_2$ wherein two germinal hydrogen atoms are replaced by $={O}$, and $L^2$ is a germinal bivalent radical comprising $C_{3-6}$cycloalkylidene, $C_{1-12}$alkylidene, $R^3$-$C_{1-6}$alkylidene, $R^4$—Y—$C_{1-6}$alkylidene and $R^5$—$Z^2$—C(=X)—$Z^1$—$C_{1-6}$alkylidene.

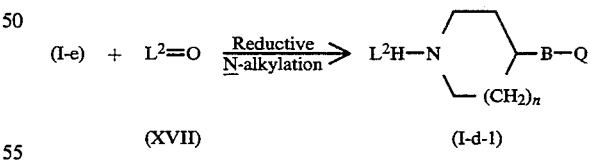

Said reductive N-alkylation can conveniently be carried out following the procedures described hereinabove for the preparation of compounds of formula (I-b) from (VII-a) and (XII), more particularly following the catalytic hydrogenation procedures.

The compounds of formula (I) wherein L is a radical of formula (c-2) and $R^4$ is aryl or Het, said $R^4$ being represented by $R^{4-a}$ and said compounds by formula (I-d-2) may also be prepared by alkylating a compound of formula (I) wherein L is a radical of formula (c-2) and $R^4$ is hydrogen, said compounds being represented by formula (I-d-3), with a reagent of formula (XVIII).

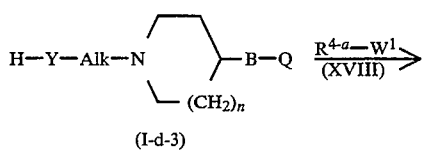

(I-d-3)

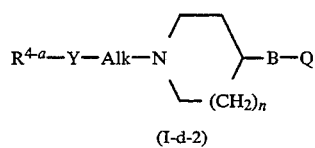

(I-d-2)

Similarly, the compounds of formula (I-d-2) may also be prepared by treating a compound of formula (I-d-4) with a reagent of formula (XIX).

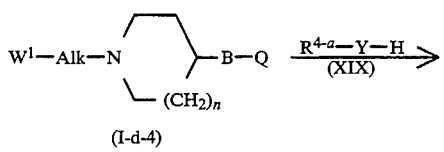

(I-d-4)

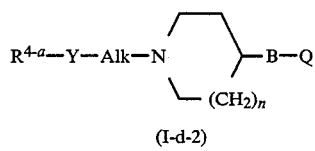

(I-d-2)

The alkylation reactions of (I-d-3) with (XVIII) and (I-d-4) with (XIX) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a dipolar aprotic solvent, e.g., N,N-dimethylformamide; N,N-dimethylacetamide; dimethyl sulfoxide; nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (c-3), $Z^1$ is NH, $Z^2$ is other than a direct bond and X is other than $NR^9$, said $Z^2$ and X being represented by $Z^{2-a}$ and $X^2$, and said compounds by (I-d-5), can be prepared by reacting an isocyanate ($X^2$=O) or isothiocyanate ($X^2$=S) of formula (XXI) with a reagent of formula (XX).

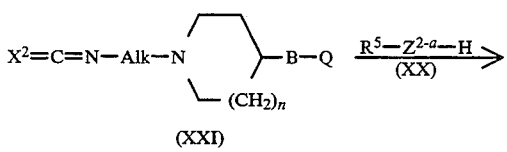

(XXI)

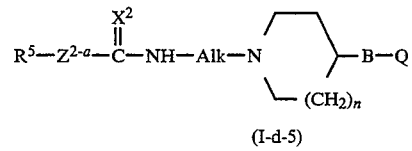

(I-d-5)

The compounds of formula (I) wherein L is a radical of formula (c-3), $Z^2$ is NH, $Z^1$ is other than a direct bond and X is other than $NR^9$, said $Z^1$ and X being represented by $Z^{1-a}$ and $X^2$, and said compounds by (I-d-6), can be prepared by reacting an isocyanate ($X^2$=O) or isothiocyanate ($X^2$=S) of formula (XXII) with a compound of formula (I-d-7).

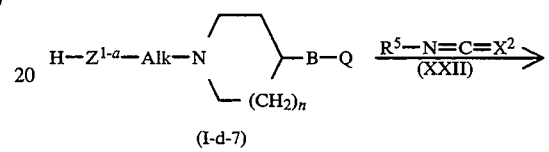

(I-d-7)

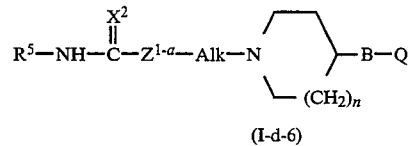

(I-d-6)

The reaction of (XX) with (XXI), or (XXII) with (I-d-7) can generally be conducted in a suitable reaction-inert solvent such as, for example, an ether, e.g., tetrahydrofuran and the like, a halogenated hydrocarbon, e.g., trichloromethane and the like. Elevated temperatures may be suitable to enhance the rate of the reaction.

The compounds of formula (I) wherein L is a radical of formula (c-3), $Z^2$ is a direct bond, $Z^1$ is other than a direct bond and X is other than $NR^9$, said $Z^1$ and X being represented by $Z^{1-a}$ and $X^2$, said compounds being represented by (I-d-8), can be prepared by reacting a reagent of formula (XXIII) or a reactive functional derivative thereof with a compound of formula (I-d-7).

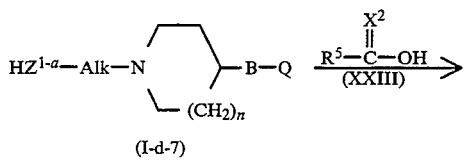

(I-d-7)

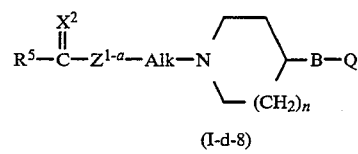

(I-d-8)

The reaction of (XXIII) with (I-d-7) may generally be conducted following art-known esterification or amidation reaction procedures. For example, the carboxylic acid may be converted into a reactive derivative, e.g., an anhydride or a carboxylic acid halide, which subsequently is reacted with (I-d-7); or by reacting (XXIII) and (I-d-7) with a suitable reagent capable of forming amides or esters, e.g., N,N-methanetetraylbis[cyclohexamine], 2-chloro-1-methylpyridinium iodide and the like. Said reactions may most conveniently be conducted in a suitable solvent such as, for example, an ether, e.g., tetrahydrofuran, a halogenated hydrocarbon, e.g., dichloromethane, trichloromethane, a dipolar aprotic solvent and the like. The addition of a base such as, for example, N,N-diethylethanamine and the like may be appropriate.

The compounds of formula (I) wherein L is a radical of formula $L^3$-$C_{2-6}$alkanediyl, said $L^3$ being aryl, Het or a radical of formula $R^5$—$Z^2$-C(=X)-, and said compounds being represented by formula (I-d-9), may also be prepared by the addition reaction of a compound of formula (I-e) to an appropriate alkene of formula (XXIV).

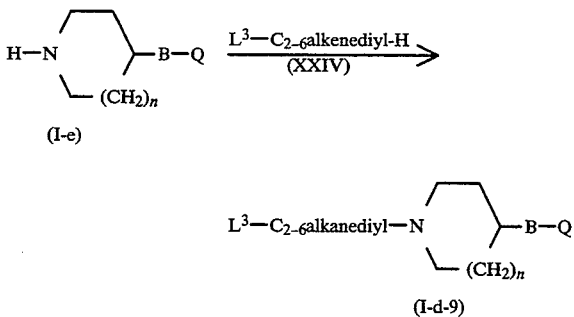

The compounds of formula (I) wherein L is 2-hydroxy-$C_{2-6}$alkyl or a radical of formula (c-4), said compounds being represented by formula (1-d-10), can be prepared by reacting a compound of formula (I-e) with an epoxide (XXV) wherein $R^{12}$ is hydrogen, $C_{1-4}$alkyl or a radical $R^6$—O—$CH_2$—.

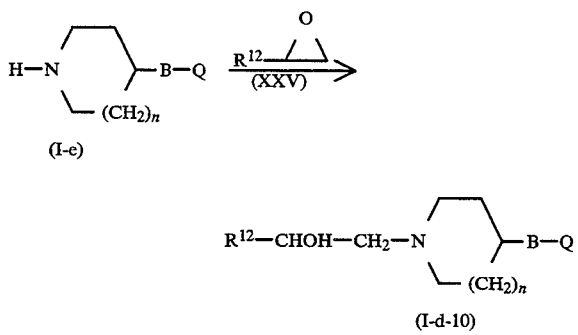

The reaction of (I-e) with respectively (XXIV) and (XXV) may be conducted by stirring and, if desired, heating the reactants in a reaction-inert solvent such as, for example, a ketone, e.g., 2-propanone, 4-methyl-2-pentanone, an ether, e.g., tetrahydrofuran, 1,1'-oxybisethane, an alcohol, e.g., methanol, ethanol, 1-butanol, a dipolar aprotic solvent, e.g., N,N-dimethylformamide, N,N-dimethylacetamide, and the like.

The compounds of formula (I) wherein $R^3$, $R^4$ or $R^5$ are Het, may also be prepared following art-known procedures for preparing heterocyclic ring systems or following analogous methods. A number of such cyclization procedures are described in for example, U.S. Pat. No. 4,695,575 and in the references cited therein, in particular U.S. Pat. No. 4,335,127; 4,342,870 and 4,443,451.

The compounds of formula (I) can also be converted into each other following artknown procedures of functional group transformation. Some examples of such procedures are cited hereinafter. The compounds of formula (I) containing a cyano substituent can be converted into the corresponding amines by stirring and, if desired, heating the starting cyano compounds in a hydrogen containing medium in the presence of an appropriate catalyst such as, for example, platinum-on-charcoal, Raney-nickel and the like catalysts. Suitable solvents are, for example, methanol, ethanol and the like. Amino groups may be alkylated or acylated following art-known procedures such as, for example, N-alkylation, N-acylation, reductive N-alkylation and the like methods. The compounds of formula (I) containing an amino group substituted with a radical arylmethyl, may be hydrogenolyzed by treating the starting compound with hydrogen in the presence of a suitable catalyst, e.g., palladium-on-charcoal, platinum-on-charcoal and the like, preferably in an alcoholic medium. The compounds of formula (I) wherein L is methyl or phenylmethyl can be converted into compounds of formula (I) wherein L is a $C_{1-6}$alkyloxycarbonyl group by reacting the methyl or phenylmethyl derivative with $C_{1-6}$alkyloxycarbonyl halides such as, for example, ethyl chloroformate in a suitable reaction-inert solvent and in the presence of a base like N,N-diethylethanamine. The compounds of formula (I) wherein L is hydrogen can be obtained from compounds of formula (I) wherein L is phenylmethyl or $C_{1-6}$alkyloxycarbonyl following art-know procedures like catalytic hydrogenation or hydrolysis in an acidic or alkaline medium depending on the nature of L.

In all of the foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds and others are new. A number of such preparation methods will be described hereinafter in more detail.

Starting materials such as the intermediates of formulae (II), (IV), (VI), (VIH), (X), (XII), (XIII) and (XV) can conveniently be prepared following procedures similar to those described in for example, U.S. Pat. Nos. 4,219,559; 4,556,660; 4,634,704; 4,695,569; 4,695,575, 4,588,722, 4,835,161 and 4,897,401 and in EP-A-0,206,415; 0,282,133; 0,297,661 and 0,307,014.

The intermediates of formula (III) can be prepared from an aromatic starting material with vicinal halo and nitro substituents (XXVII) by reaction with a suitable amine of formula (XXVI), followed by art-known nitro-to-amine reduction.

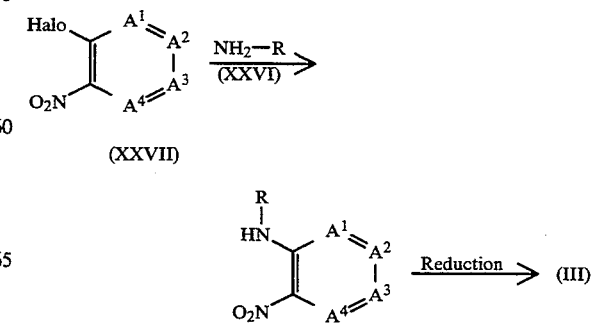

The intermediates of formulae (V), (VII), (IX) and (XI) then, can be prepared from the intermediates of formula (III) following art-known procedures of converting aromatic products with vicinal amino groups into benzimidazoles, imidazopyridines and/or purines.

The compounds of formula (I), the pharmaceutically acceptable acid addition salts and stereochemically isomeric forms thereof possess useful pharmacological properties. More particularly, they are active antiallergic and antihistaminic compounds which activity can be demonstrated by, e.g., the results obtained in the test "Protection of Rats from Compound 48/80-induced lethality", the "PCA (passive cutane anaphylaxis)-test in Rats" described in Drug Dev. Res., 5, 137–145 (1985), the "Histamine-induced lethality test in Guinea Pigs" and the "Ascaris Allergy test in Dogs". The latter two tests are described in Arch. Int. Pharmacodyn. Ther. 251, 39–51 (1981).

An interesting feature of the present compounds resides in their rapid onset of action and favorable duration of action.

In view of their antiallergic properties, the compounds of formula (I) and their acid addition salts are very useful in the treatment of broad range of allergic diseases such as, for example, allergic rhinitis, allergic conjunctivitis, chronic urticaria, allergic: asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carders such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carder comprises saline solution, glucose solution or a mixture of saline and glucose solution. Injectable suspensions may also be prepared in which case appropriate liquid carders, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carder. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) or a pharmaceutically acceptable acid addition salt form thereof.

Those of skill in treating allergic diseases in warm-blooded animals could easily determine the effective amount from the test results presented hereinafter. In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects. Unless otherwise stated all parts therein are by weight.

Experimental Part

A. Preparation of the Intermediates

Example 1

To a mixture of 15.5 pans of 2-chloro-1H-benzimidazole and 235 parts of N,N-dimethylacetamide there were added 22 pans of 4-(chloromethyl)-2-methylthiazole monohydrochloride and 25.4 pans of sodium carbonate. The whole was stirred for 18 hours at 75° C. and was then poured into water. The product was extracted with 4-methyl-2-pentanone and the extract was washed with water, dried, filtered and evaporated. The residue was crystallized from 2,2'-oxybispropane, yielding 11.3 parts (42.8%) of 2-chloro-1-[(2-methyl-4-thiazolyl)methyl]-1H-benzimidazole (interm. 1). In a similar manner there was also prepared 2-chloro-1-[(6-methyl-2-pyridinyl)methyl]1H-benzimidazole (interm. 2).

Example 2 a) To a stirred and refluxing mixture of 60 pans of 4-fluorobenzenethiol, 93 pans of 1-bromo-3-chloropropane, 100 parts of ethanol and 45 parts of water there was added dropwise a solution of 19 parts of sodium hydroxide in 80 pans of water. Stirring at reflux temperature was continued for 8 hours. After cooling, the organic layer was separated and distilled under reduced pressure (1.7 103 Pa), yielding two fractions of resp. 53 parts (bp. 136°–140° C.) and 32 pans (bp. 140°–152° C.) of product. Total yield: 85 parts of 1-[(3-chloropropyl)-thio]-4-fluorobenzene (interm. 3).

b) A mixture of 67.5 parts of intermediate 3; 42.9 parts of 1,4-dioxa-8-azaspiro[4,5]decane, 47.7 parts of sodium carbonate, a few crystals of potassium iodide and 2400 parts of 4-methyl-2-pentanone was stirred for 70 hours at reflux temperature. The reaction mixture was filtered while hot and the filtrate was washed with 1,1'-oxybisethane and evaporated. The residue was triturated in 2,2'-oxybispropane while cooling at −20° C. A first fraction of 4.4 parts of product was obtained by filtration. Evaporation of the mother liquor yielded a second fraction of 97 parts of product. Total yield: 101.4 parts of 1,4-dioxa-8-[3-[(4-fluorophenyl)thio]propyl]-8-azaspiro[4,5]decane; mp. 135.5°–140° C. (interm. 4)

Example 3 a) A mixture of 2.44 parts of 6-methyl-2-pyridinemethanamine, 3.2 parts of 2-chloro-3nitropyridine, 1.7 parts of sodium hydrogen carbonate and 120 parts of ethanol was stirred for 3 hours at reflux temperature. The reaction mixture was filtered while hot over diatomaceous earth. After cooling, the precipitate which formed in the tiltrate was filtered off and dried, yielding 2.5 parts (51%) of 6-methyl-N-(3-nitro-2-pyridinyl)-2pyridinemethanamine; mp. 131.7° C. (interm. 5).

b) A mixture of 55 parts of intermediate 5; 2 parts of a solution of thiophene in methanol 4% and 480 parts of methanol was hydrogenated at normal pressure and at 50° C. with 3 parts of platinum-on-charcoal catalyst 5%. After the calculated amount of hydrogen was taken up, the catalyst was filtered off over diatomaceous earth and the tiltrate was evaporated, yielding 47 parts (99.7%)of N$^2$-[(6-methyl-2-pyridinyl)methyl]-2,3-pyridinediamine (interm. 6).

c) A mixture of 47 parts of ethyl 4-isothiocyanato-1-piperidinecarboxylate, 47 parts of intermediate 6 and 900 parts of tetrahydrofuran was stirred overnight at room temperature. There was added 2,2'-oxybispropane to enhance crystallization. The product was filtered off and dried, yielding 78.5 parts (83.5%) of ethyl 4-[[[[2-[[(6-methyl-2pyridinyl)methyl]amino]-3-pyridinyl]aminolthioxomethyl]amino]-1-piperidinecarboxylate; mp. 176° C. (interm. 7).

B. Preparation of the Final Compounds

Example 4

To a stirred mixture of 45 parts of 2-[[1-(phenylmethyl)-4-piperidinyl]methyl]-1H-benzimidazole and 376 parts of N,N-dimethylformamide there were added portionwise 12.2 parts of a dispersion of sodium hydride in mineral oil (60%) and, after stirring for ½ hour, a solution of 28 parts of 2-(chloromethyl)-6-methylpyridine monohydrochloride in some N,N-dimethylformamide. Stirring at room temperature was continued overnight. After the addition of ethanol, the reaction mixture was poured into water. The product was extracted with methylbenzene and the extract was dried, filtered and evaporated. The residue was purified by column chromatography (silica gel; CH$_2$Cl$_2$/CH$_3$OH 95:5). The eluent of the desired fraction was evaporated and the residue was converted into the ethanedioate (1:5/2) salt in acetonitrile. The product was filtered off and dried, yielding 27.8 parts (29.2%) of 1-[(6-methyl-2-pyridinyl)methyl]-2-[[1-(phenylmethyl)-4-piperidinyl]methyl]-1H-benzimidazole ethanedioate (1:5/2); mp. 155.3° C. (comp. 48).

Example 5

To a stirred mixture of 36.7 parts of compound 48 and 267 parts of tetrahydrofuran there were added 15.68 parts of ethyl chloroformate. Stirring was continued for 6 hours and then there were added 11.7 parts of N,N-diethylethanamine. After stirring over weekend, the reaction mixture was evaporated and the residue was taken up in water. The product was extracted with dichloromethane and the extract was dried, filtered and evaporated. The residue was purified by column chromatography (silica gel; CH$_2$Cl$_2$/CH$_3$OH 95:5). The eluent of the desired fraction was evaporated and the residue was crystallized from acetonitrile. The product was filtered off and dried, yielding 15.65 parts (44.3%) of ethyl 4-[[1-[(6-methyl-2-pyridinyl)methyl]-1H-benzimidazol-2-yl]methyl]-1-piperidinecarboxylate; mp. 159.7° C. (comp. 53).

Example 6

A mixture of 2.9 parts of ethyl 4-[(1H-benzimidazol-2-yl)amino]-1-piperidinecarboxylate, 1.8 parts of 4-(chloromethyl)-2-methylthiazole monohydrochloride, 2.12 pans of sodium carbonate and 45 parts of N,N-dimethylacetamide was stirred overnight at 70° C. The reaction mixture was poured into water and the product was extracted with 4-methyl-2-pentanone. The extract was dried, filtered and evaporated and the residue was crystallized from acetonitrile. The product was filtered off and dried, yielding 1.5 parts (37.5%) of ethyl 4-[[1-[(2-methyl-4-thiazolyl)methyl]-1H-benzimidazol-2-yl]amino]-1-piperidinecarboxylate; mp. 160° C. (comp. 12).

Example 7

A mixture of 25 parts of compound 12; 34 parts of potassium hydroxide and 160 parts of 2-propanol was stirred overnight at reflux temperature. The reaction mixture was evaporated and the residue was taken up in water. The product was extracted with dichloromethane and the extract was dried, filtered and evaporated. The residue was convened into the trihydrochloride salt in 2-propanol. The product was filtered off and dried, yielding 20 parts (71.2% ) of 1-[(2-methyl-4-thiazolyl)methyl]—N-(4-piperidinyl)1H-benzimidazol-2-amine trihydrochloride hemihydrate; mp. 206.4° C. (comp. 13).

Example 8

A mixture of 15 parts of compound 58 and 224 parts of hydrobromic acid 48% was refluxed for 3 hours. The reaction mixture was evaporated and the residue was taken up in water. After basifying with sodium hydroxide solution, the product was extracted with dichloromethane. The extract was dried, filtered and evaporated. The residue was crystallized from acetonitrile, yielding 5 parts (41.3%) of 1-[(4-methyl-2-thiazolyl)methyl]-N-(4-piperidinyl)-1H-benzimidazol-2-amine (comp. 59).

Example 9

A mixture of 2.3 parts of 6-(2-chloroethyl)-7-methyl-5H-thiazolo[3,2-a]pyrimidin-5one, 3.3 parts of compound 13; 1.6 parts of sodium carbonate and 160 parts of -methyl-2-pentanone was stirred for 48 hours at reflux temperature. The reaction mixture was evaporated and the residue was taken up in water. The product was extracted with dichloromethane and the extract was dried, filtered and evaporated. The residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried, yielding 1.64 parts (31.6%) of 7-methyl-6-[2-[4-[[1-[(2-methyl-4-thiazolyl)methyl]-1H-benzimidazol-2-yl]amino]-1-piperidinyl]ethyl]-5H-thiazolo[3,2-a]pyrimidin-5-one; mp. 129.8° C. (comp. 18).

Example 10

A mixture of 2.26 parts of 3-(2-chloroethyl)-2-methyl-4H-pyrido[1,2-a]pyrimidin-4one, 3.2 pans of compound 2; 1.06 parts of sodium carbonate and 45 pans of N,N- dimethylacetamide was stirred overnight at 70° C. The reaction mixture was poured into water. The precipitate was filtered off and boiled in methanol. The product was filtered off while hot, yielding 2.1 parts (41.5%) of 2-methyl-3-[2-[4-[[3-[(6-methyl-2pyridinyl)methyl]-3H-imidazo[4,5-b]pyridin-2-yl]amino]-1-piperidinyl]ethyl]-4H-pyrido [1,2-a]pyrimidin-4-one; mp. 233.1 ° C. (comp. 7).

Example 11

The following reaction was carded out under a nitrogen atmosphere. To a mixture of 7.5 parts of ethyl 4-hydroxy-1-piperidinecarboxylate and 94 parts of N,N-dimethylformamide there were added portionwise 2.1 parts of a dispersion of sodium hydride in mineral oil (50%). After stirring for 1 hour at room temperature and for 20 min at 40° C, there was added dropwise a solution of 11.3 parts of intermediate 1 in 94 parts of N,N-dimethylformamide. Stirring was continued overnight at room temperature. After addition of some ethanol, the reaction mixture was evaporated. The residue was poured into ice-water and the whole was extracted with dichloromethane. The extract was dried, filtered and evaporated. The residue was purified by column chromatography (silica gel; $CH_2Cl_2/CH_3OH$ 90:10). The eluent of the desired fraction was evaporated, yielding 13 parts (75.5%) of ethyl 4-[[1-[(2-methyl-4-thiazolyl)methyl]-1H-benzimidazol-2-yl]-oxo]-1-piperidinecarboxylate (comp. 20).

Example 12

A mixture of 4.5 pans of compound 13; 2 pans of polyoxymethylene, 5 parts of potassium acetate and 120 parts of methanol was hydrogenated at normal pressure and at 50° C. with 1 part of palladium-on-charcoal catalyst 10%. After the calculated amount of hydrogen was taken up, the catalyst was filtered off over diatomaceous earth. The filtrate was evaporated and the residue was taken up in water. After basifying with sodium carbonate, the product was extracted with trichloromethane. The extract was dried, filtered and evaporated and the residue was convened into the ethanedioate (1:2) salt in methanol. The product was filtered off and dried, yielding 3.7 pans (70.9%) of N-(1-methyl-4-piperidinyl)-1-[(2-methyl-4-thiazolyl)methyl]-1H-benzimidazol-2-amine ethanedioate (1:2); mp. 221.3° C. (comp. 16).

Example 13

A mixture of 78 parts of intermediate 7; 58.5 parts of mercury(II)oxide, 1 part of sulfur and 800 parts of ethanol was stirred for 2 hours at reflux temperature. The reaction mixture was filtered over diatomaceous earth and the filtrate was evaporated, yielding 63.5 parts (88.5%) of ethyl 4-[[3-[(6-methyl-2-pyridinyl)methyl]-3H-imidazo[4,5-b]-pyridin-2-yl]amino]-1-piperidinecarboxylate (comp. 1).

Example 14

Trough a stirred mixture of 3.23 pans of compound 2 and 80 parts of methanol there were bubled 0.9 parts of oxirane. Stirring was continued overnight at room temperature. The reaction mixture was evaporated and the residue was purified by column chromatography (silica gel; $CHCl_3/CH_3OH$ 96:4). The eluent of the desired fraction was evaporated and the residue was crystallized from acetonitrile. The product was filtered off and dried, yielding 0.7 parts (19%) of 4-[[3-[(6-methyl-2-pyridinyl)methyl]-3H-imidazo [4,5-b]-pyridin-2-yl]amino]-1-piperidineethanol; mp. 152.0° C. (comp. 4).

Example 15

A mixture of 9 parts of compound 5; 11 parts of potassium hydroxide and 120 parts of 2-propanol was stirred for 4 hours at reflux temperature. The reaction mixture was evaporated and the residue was taken up in water. The product was extracted with dichloromethane (2x) and the combined extracts were dried, filtered and evaporated, yielding 7.5 parts (100% ) of N-[1-(2-aminoethyl)-4-piperidinyl]-3-[(6-methyl-2-pyridinyl)-methyl]-3H-imidazo[4,5-b]pyridin-2-amine (comp. 8).

Example 16

A mixture of 1.2 parts of 2-chloropyrimidine, 3.7 parts of compound 8; 0.9 parts of sodium hydrogen carbonate and 80 parts of ethanol was stirred overnight at reflux temperature. The reaction mixture was filtered over diatomaceous earth and the filtrate was evaporated. The residue was crystallized from a mixture of acetonitrile and methanol. The product was filtered off and dried in vacuo at 130° C. overnight, yielding 1 part (22.5%) of 3-[(6-methyl-2-pyridinyl)methyl]-N-[1-[2-[(2-pyrimidinyl)amino]ethyl]-4-piperidinyl]-3H-imidazo[4,5-b]pyridin-2-amine; mp. 187.4° C. (comp. 9).

All compounds listed in tables 1, 2, 3, 4 and 5 were prepared following methods of preparation described in examples 4–16, as is indicated in column 2 (Ex. No.)

TABLE 1

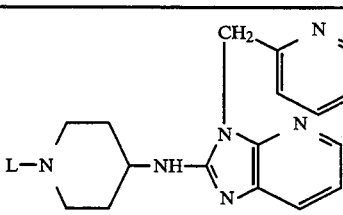

| Comp. No. | Ex. No. | L | Physical data |
|---|---|---|---|
| 1 | 13 | $CH_3$—$CH_2$—OOC— | — |
| 2 | 7 | H— | 147.6° C./ $H_2O(1:1/2)$ |
| 3 | 12 | $CH_3$— | 130.5° C. |
| 4 | 14 | HO—$(CH_2)_2$— | 152.0° C. |
| 5 | 10 | $CH_3$—$CH_2$—OOC—NH—$(CH_2)_2$— | 139.6° C. |
| 6 | 10 | $CH_3O$—$C_6H_4$—$(CH_2)_2$— | 142.3° C. |
| 7 | 10 | 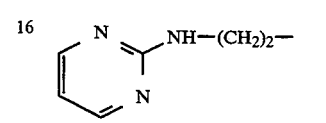 | 233.1° C. |
| 8 | 15 | $NH_2$—$CH_2$—$CH_2$— | — |
| 9 | 16 | 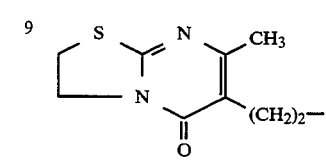 | 187.4° C. |
| 10 | 9 | 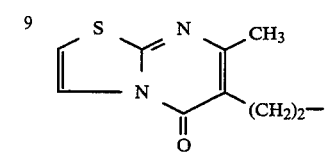 | 185.4° C. |
| 11 | 9 | (same structure with S) | 215.5° C. |

TABLE 2

[Structure: L-N-piperidine-B-benzimidazole core with 2-(methylthio)-CH=C-CH2- substituent bearing CH3 and N groups]

| Comp. No. | Ex. No. | L | B | Physical data (mp.-salt) |
|---|---|---|---|---|
| 12 | 6 | CH₃—CH₂—OOC— | NH | 160° C. |
| 13 | 7 | H | NH | 206.4° C./HCl (1:3)/H₂O (1:1/2) |
| 14 | 10 | CH₃—CH₂—O—(CH₂)₂— | NH | 201.6° C./(COOH)₂ (1:2) |
| 15 | 10 | CH₃O—C₆H₄—(CH₂)₂— | NH | 228.5° C./HCl (1:2)/H₂O |
| 16 | 12 | CH₃— | NH | 221.3° C./(COOH)₂ (1:2) |
| 17 | 9 | [thiazine-pyrimidinone with CH3, (CH2)2—] | NH | 185.4° C. |
| 18 | 9 | [thiazine-pyrimidinone with CH3, (CH2)2—] | NH | 129.8° C. |
| 19 | 9 | [thiazine-pyrimidinone with CH3, (CH2)2—] | NH | 186.1° C. |
| 20 | 11 | CH₃—CH₂—OOC— | O | — |
| 21 | 7 | H | O | 127.7° C. |
| 22 | 9 | [thiazine-pyrimidinone with CH3, (CH2)2—] | O | 137.0° C. |
| 23 | 9 | [thiazine-pyrimidinone with CH3, (CH2)2—] | O | 160.4° C. |
| 24 | 4 | C₆H₅—CH₂— | CH₂ | 115.1° C. |
| 25 | 5 | CH₃—CH₂—OOC— | CH₂ | 125.0° C. |
| 26 | 7 | H | CH₂ | 155.9° C. |
| 27 | 9 | [thiazine-pyrimidinone with CH3, (CH2)2—] | CH₂ | 150.7° C. (E)-2-butenedioate (1:3/2) 2-propanolate(1:1) |
| 28 | 9 | [thiazine-pyrimidinone with CH3, (CH2)2—] | CH₂ | 153.4° C. |

TABLE 2-continued

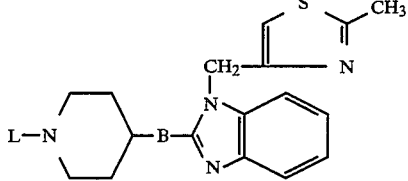

| Comp. No. | Ex. No. | L | B | Physical data (mp.-salt) |
|---|---|---|---|---|
| 29 | 9 | (structure: S-C(=N)-N ring with CH₃, (CH₂)₂—, C=O) | CH₂ | 179.9° C. |

TABLE 3

| Comp. No. | Ex. No. | L | B | Physical data (mp.-salt) |
|---|---|---|---|---|
| 30 | 6 | $CH_3-CH_2-OOC-$ | NH | 155.1° C. |
| 31 | 7 | H— | NH | 239.2° C. |
| 32 | 9 | (thiazine-type structure with CH₃, (CH₂)₂—, C=O) | NH | 196.7° C. |
| 33 | 9 | (thiazoline structure with CH₃, (CH₂)₂—, C=O) | NH | 204.2° C. |
| 34 | 9 | (structure with CH=CH, CH₃, (CH₂)₂—, C=O) | NH | 125.5° C. |
| 35 | 4 | $C_6H_5-CH_2-$ | CH₂ | 119.6° C. |
| 36 | 5 | $CH_3-CH_2-OOC-$ | CH₂ | 101.3° C. |
| 37 | 7 | H— | CH₂ | — |
| 38 | 9 | (thiazoline structure with CH₃, (CH₂)₂—, C=O) | CH₂ | 161.7° C./H₂O (1:1/2) |
| 39 | 9 | (structure with CH=CH, CH₃, (CH₂)₂—, C=O) | CH₂ | 158.5° C./H₂O (1:3/2) |

TABLE 3-continued

[Structure: L—N(piperidine)—B—benzimidazole with CH₂ linker to thiazole-like ring with N, S, CH₃]

| Comp. No. | Ex. No. | L | B | Physical data (mp.-salt) |
|---|---|---|---|---|
| 40 | 9 | [pyrido-pyrimidinone with CH₃ and (CH₂)₂—] | CH₂ | 171.0° C. |
| 41 | 9 | [pyrido-pyrimidinone with CH₃ and (CH₂)₂—] | NH | 219.8° C. |
| 42 | 12 | H₃C— | NH | 114.6° C./H₂O (1:3/2) |
| 43 | 9 | CH₃O—C₆H₄—(CH₂)₂— | NH | 103.1 C. |

TABLE 4

[Structure: L—N(piperidine)—B—benzimidazole with CH₂ linker to pyridine with CH₃]

| Comp. No. | Ex. No. | L | B | Physical data (mp.-salt) |
|---|---|---|---|---|
| 44 | 6 | CH₃—CH₂—OOC— | NH | 182.6° C. |
| 45 | 7 | H | NH | 161.0° C./H₂O (1:1/2) |
| 46 | 9 | [thiazine-fused pyrimidinone with CH₃ and (CH₂)₂—] | NH | 206.6° C. |
| 47 | 9 | [thiazine-fused pyrimidinone with CH₃ and (CH₂)₂—] | NH | 225.3° C. |
| 48 | 4 | C₆H₅—CH₂— | CH₂ | 155.3° C./(COOH)₂ (1:5/2) |
| 49 | 9 | [thiazine-fused pyrimidinone with CH₃ and (CH₂)₂—] | NH | 131.9° C./H₂O |
| 50 | 11 | CH₃—CH₂—OOC— | O | — |
| 51 | 7 | H | O | 106.9° C. |

TABLE 4-continued
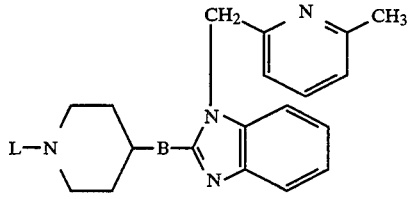
| Comp. No. | Ex. No. | L | B | Physical data (mp.-salt) |
|---|---|---|---|---|
| 52 | 9 | 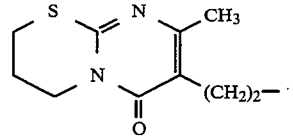 | O | 144.0° C. |
| 53 | 5 | CH₃—CH₂—OOC— | CH₂ | 159.7° C. |
| 54 | 7 | H | CH₂ | — |
| 55 | 9 | 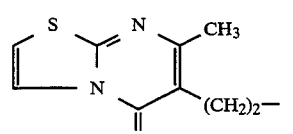 | CH₂ | 176.1° C. |
| 56 | 9 | 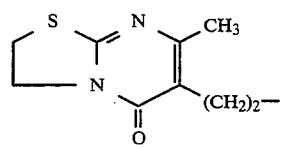 | CH₂ | 222.5° C. (E)-2-butenedioate(1:1) |
| 57 | 9 | 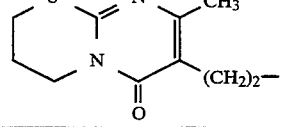 | CH₂ | 160.6° C. (E)-2-butenedioate(1:3/2) 2-propanolate(1:1) |
TABLE 5
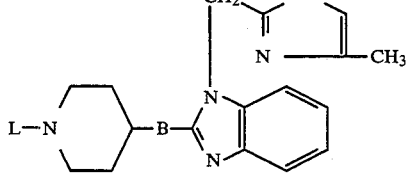
| Comp. No. | Ex. No. | L | B | Physical data (mp.-salt) |
|---|---|---|---|---|
| 58 | 6 | CH₃—CH₂—OOC— | NH | 183.6° C. |
| 59 | 8 | H— | NH | — |
| 60 | 9 | 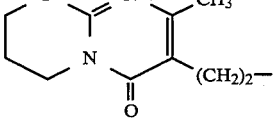 | NH | 147.7° C./H₂O |
| 61 | 9 | 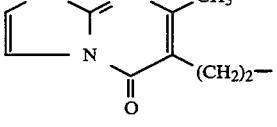 | NH | 215.5° C. |
| 62 | 12 | CH₃— | NH | 128.5° C./H₂O (1:1/2) |

TABLE 5-continued

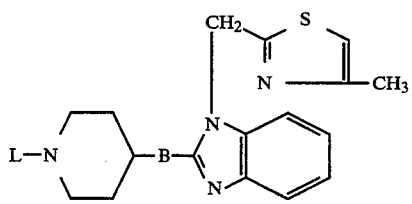

| Comp. No. | Ex. No. | L | B | Physical data (mp.-salt) |
|---|---|---|---|---|
| 63 | 9 | (structure: thiazine-pyridone with CH₃ and (CH₂)₂—) | NH | 196.7° C. |
| 64 | 9 | $CH_3O-C_6H_4-(CH_2)_2-$ | NH | 109.9° C. |
| 65 | 4 | $C_6H_5-CH_2-$ | $CH_2$ | 129.5° C. |
| 66 | 5 | $CH_3-CH_2-OOC-$ | $CH_2$ | — |
| 67 | 7 | H— | $CH_2$ | — |
| 68 | 9 | (structure: thiazine-pyridone with CH₃ and (CH₂)₂—) | $CH_2$ | 126.6° C. |
| 69 | 9 | (structure: thiazoline-pyridone with CH₃ and (CH₂)₂—) | $CH_2$ | 170.4° C. |
| 70 | 9 | (structure: thiazine-pyridone with CH₃ and (CH₂)₂—) | $CH_2$ | 176.9° C. (Z)-2-butenedioate(1:2) |
| 71 | 9 | (structure: pyridine-pyridone with CH₃ and (CH₂)₂—) | $CH_2$ | 158.8° C. |

C. Pharmacological Example

Example 17

The useful anti-allergic and anti-histaminic properties of the compounds of formula (I) can be demonstrated, e.g., in the test "Protection of rats from compound 48/80 induced lethality" which is described in U.S. Pat. No. 4,556,660. The compounds of formula (I) were administered subcutaneously and/or orally to rats. The ED$_{50}$-value (mg/kg) for the compounds 9, 16, 19, 23, 27, 28, 29, 55, 62, 69 and 70 was found to be 0.04 mg/kg.

We claim:

1. A compound of the formula:

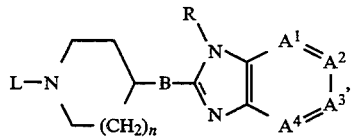

(I)

a pharmaceutically acceptable addition salt or a stereochemically isomeric form thereof, wherein:

—$A^1$=$A^2$—$A^3$=$A^4$— represents a bivalent radical having the formula:

—CH=CH—CH=CH— (a-1), wherein one or two hydrogen atoms in said radical (a-1) may each independently be replaced by halo, $C_{1-6}$alkyl, $C_{1-6}$alkyloxy, hydroxy or trifluoromethyl;

B represents NH or $CH_2$;

R represents a radical of the formula:

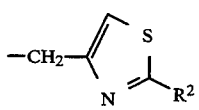

(b-1-c)

or

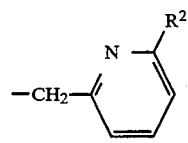 (b-2-b)

wherein R² is C$_{1-4}$alkyl;

n is 1; and

L represents hydrogen, C$_{1-4}$alkyl or a radical of the formula:

-Alk—R³ (c-1);

wherein:
each Alk individually represents C$_{1-6}$alkanediyl; and
R³ represents phenyl or C$_{1-4}$alkyloxyphenyl 2. A compound according to claim 1 wherein: R² represents methyl.

3. An antiallergic composition comprising a pharmaceutically acceptable carrier and as active ingredient an effective antiallergic amount of a compound as claimed in claim 1.

4. A method of treating warm-blooded animals suffering from allergic diseases comprising administering to said warm-blooded animals an effective antiallergic amount of a compound as claimed in claim 1.

* * * * *